United States Patent [19]

Maeda et al.

[11] Patent Number: 4,670,607
[45] Date of Patent: Jun. 2, 1987

[54] METHOD FOR PRODUCING 2-(SUBSTITUTED ARYL) PROPIONALDEHYDE

[75] Inventors: Sadayuki Maeda, Nara; Yasutaka Shinoo, Yonezawa; Shinji Takenaka, Yao; Susumu Arashida, Settsu; Iwao Shimizu, Yonezawa, all of Japan

[73] Assignee: Hamari Chemicals, Ltd., Osaka, Japan

[21] Appl. No.: 864,432

[22] Filed: May 16, 1986

[30] Foreign Application Priority Data

Oct. 29, 1985 [JP] Japan .................. 60-242411
Oct. 29, 1985 [JP] Japan .................. 60-242413

[51] Int. Cl.⁴ .............................. C07C 45/58
[52] U.S. Cl. .................................. 568/427
[58] Field of Search .......................... 568/427

[56] References Cited

U.S. PATENT DOCUMENTS 2,628,255  2/1953  Sexton et al. .................. 568/427

OTHER PUBLICATIONS

Franzen et al, Tetrahedron Letters No. 15 (1962) 661-662.
Franzen et al, Berichte (1963) 1881-1890.

*Primary Examiner*—Bernard Helfin
*Attorney, Agent, or Firm*—Burgess, Ryan & Wayne

[57] ABSTRACT

A 2-(substituted aryl)propionaldehyde of the formula,

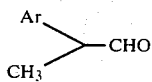

(wherein Ar denotes

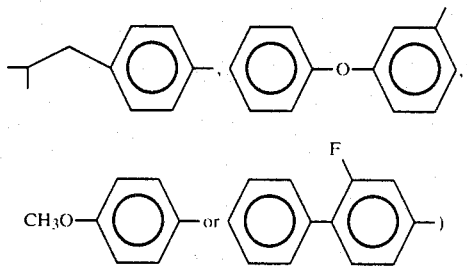

is produced in high yield by reacting a methyl (substituted aryl) ketone of the formula

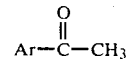

with phenyldimethylsulfonium methylsulfate of the formula,

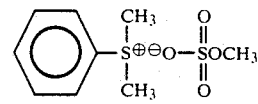

in the presence of alkali metal hydroxide to obtain a reaction mixture containing 2-(substituted aryl)1,2-epoxypropane of the formula,

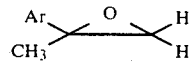

and thioanisole, and subjecting the reaction mixture to contact with anhydrous $MgCl_2$. The propionaldehyde compound is also produced in high yield by contacting the epoxypropane compound with anhydrous $MgCl_2$ in the presence of a soft nucleophile such as a sulfide, a thiol and a phosphine.

13 Claims, No Drawings

METHOD FOR PRODUCING 2-(SUBSTITUTED ARYL) PROPIONALDEHYDE

This invention relates to a method of producing a 2-(substituted aryl)propionaldehyde of the formula:

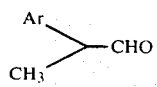

(wherein Ar denotes

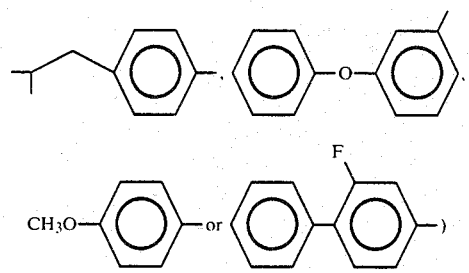

The compounds obtained by this invention are very useful intermediates in the production of 2-(substituted aryl)propionic acids which are useful as anti-inflammatory agents.

With regard to the production of 2-(substituted aryl)propionaldehyde, various reports have been suggested. Namely, there are known, for instance, (1) a method, wherein a glycidyl acid ester is hydrolyzed to a glycidyl acid metal salt and then subjected to decarboxylation to give an aldehyde derivative [Japanese Patent Application Publication (hereinafter abbreviated as J.P.A. Pub.) No. 24550/1972], (2) a method wherein a glycidyl acid ester is treated with an acid to give a 2-(substituted aryl)propionaldehyde and 3-methyl-3-(substituted aryl)pyruvic acid (J.P.A. Pub. Nos. 35069/1978 and 41976/1984), (3) a method wherein 2-hydroxy-3-(substituted aryl)-3-butene acid ester is treated with an acid (J.P.A. Pub. No. 37183/1975), (4) A method wherein a substituted arylethylene is allowed to react with hydrogen and carbon monoxide in the presence of a catalyst, rhodium compound [Japanese Patent Application Disclosure (hereinafter abbreviated as J.A.P. Dis.) No. 2483/1979], (5) a method wherein methyl-(substituted pheny)ketone is allowed to react with dimethylsulfonium methylide or dimethyloxosulfonium methylide to give 2-(substituted aryl)-1,2-epoxide which is then subjected to isomerization in the presence of an acid catalyst (J.P.A. Dis. No. 100040/1976), (6) a method wherein methyl-(substituted aryl)ketone is allowed to react with trimethylsulfonium methylsulfate in the presence of a base to give 2-(substituted aryl)-2-methyloxirane which is then subjected to isomerization with an acid (J.P.A. Dis. Nos. 128933/1976, 154428/1981; J.P.A. Pub. Nos. 40701/1981 and 29482/1979) and (7) a method wherein chloromethyl-(substituted phenyl)ketone is allowed to react with a Grignard reagent to give 2-(substituted phenyl)-2-hydroxy-1-chloropropane which is then allowed to react with an alkali to give 2-(substituted phenyl-1,2-epoxypropane and further a ring-opening reaction is carried out employing anhydrous zinc chlorode. (J.P.A. Pub. No. 46829/1978) etc.

In the methods (1) and (2), the starting material is not necessarily easily available, and the yield of the aldehyde compound is low, therefore, the methods are not suitable for industrial production.

The method (3) requires many steps to synthesize the starting material, 2-hydroxy-3-(substituted aryl)-3-butene acid ester and the total yield of the method is low.

In the method (4), it is very difficult to obtain or produce the starting material, arylethylene, and a high pressure of 160–200 kg/cm$^2$ is necessary to produce the material, therefore, this method can not be employed in large scale.

In the method (5), it is necessary to react sodium hydroxide, sodium amide, potssium-t-butoxide or sodium methylate etc. with trimethyl(or trimethyloxo)sulfonium salt in order to produce dimethylsulfonium methylide or dimethyloxosulfonium methylide. The above bases are, however, so unstable that sodium hydride or sodium amide is ignited explosively with water and a alkali metal alcoholate such as sodium methylate remarkably loses its activity even with a slight amount of water. Therefore, it is necessary to carry out the reaction under anhydrous condition which makes the reaction difficult to handle.

In the method (6), sodium methylate is employed and it gives the same problem as the above method (4).

In the case of reacting dimethylsulfonium methylide in the method (5) and in the reaction process of the method (6), there is generated inevitably dimethylsulfide having a strong bad smell and inflammability which disperses rapidly because of its low boiling point of 37.5°–38° C. Therefore, these methods give problems in environmental sanitationand safety, when employed in industrial scale.

In the method (7), the starting material, chloromethyl-(substituted phenyl)ketone, is hardly available and the reactions in the method requires three reactions with complicated procedures. Furthermore, the Grignard reagent itself is expensive and the use of the reagent requires special equipment and caution to prevent accidents.

In addition to the foregoing, a reaction wherein 2-(substituted aryl)-1,2-epoxypropane is isomerized to 2-(substituted aryl)propionaldehyde in the presence of an acid catalyst is well known hitherto. This reaction usually carried out at a relatively high temperature.

According to independent experiments performed by the present inventors, the above reaction condition inevitably causes the formation of by-products, an aryl alcohol compound (V) produced by heat-isomerization and a polymer having undetermined structure.

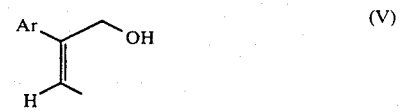

If a strong acidic catalyst such as sulfuric acid, anhydrous aluminum chloride, boron trifluoride or anhydrous zinc chloride is employed, the high temperature condition can be avoided, however, the reaction mixture generates intensive heat by its exothermic reaction, making the mixture colored and resulting in a great amount of by-products.

Furthermore, with regard to the methods of converting methyl(substituted aryl)ketone to 2-(substituted aryl)1,2-epoxypropane, the following reports have been published:

In Tetrahedron Letters, 1979, 203–206 (1979), it is proposed that a ternary phase be formed by suspending a dimethylpolystyrylsulfonium salt in a mixture of dichloromethane and aqueous sodium hydroxide, followed by reaction with acetophenone in the presence of a phase transfer catalyst such as tetrabutylammonium hydroxide, for epoxidation of acetophenone.

However, one day is required for the reaction to be completed. The starting material for preparing the sulfonium salt, namely polystyrene sulfide, is not readily available. Even if it is available, it is required in a relatively large quantity as compared with the ketone compound and the recovery and reuse of said polymer requires conversion of a large quantity of the sulfide to a sulfonium salt. The phase transfer catalyst is expensive and difficult to recover.

Tetrahedron Lett., 1982, 5283–5286 (1982) described conversion of acetophenone to the corresponding epoxycompound by reaction with a trimethylsulfonium salt in acetonitrile in the presence of potassium hydroxide. However, the yield is only 38%. Independent experiments performed by the present inventors have confirmed this low yield.

On the other hand, the reaction which converts ketones to epoxides using a phenyldimethylsulfonium salt is reported in Tetrahedron Lett., 1962, 661–662 (1962); Ber., 1881–1890 (1963), and J. Organometal. Chem., 191, C4–C6 (1979), among others. In all the procedures described, potassium tertbutoxide is used as the base and dimethyl sulfate as the solvent. The base offers various problems, as already mentioned hereinabove, while this solvent is relatively expensive. Furthermore, 2-(substituted aryl)-1,2-epoxypropane is inherently unstable to heat, easily isomerized to an arylalcohol compound and converted to a polymer of undetermined structure, as mentioned previously.

According to a test performed by the present inventors, the purity deterioration rates of 2-(4-isobutylphenyl)-1,2-epoxypropane are 2.4% in the case of heating at 60°–70° C. for 5 hours, 10.7% at 80°–90° C. for 5 hours and 13.7% at 110° C. for 5 hours.

Therfore, it is desirable to avoid heating as far as possible in the processes of extracting, concentrating and purifying the epoxypropane compound from the reaction mixture. Particularly, in case that the compound is distilled, it is to be conducted under high vacuum.

The present inventors, who are not satisfied with the above-mentioned prior arts, conducted studies to find out a method of producing 2-(substituted aryl)propionaldehyde safely and advantageously at low cost.

As a result, the studies lead to the following findings: that 2-(substituted aryl)-1,2-epoxypropane is readily formed in high yields in one step when methyl(substituted aryl)ketone is reacted with phenyldimethylsulfonium methyl sulfate in the presence of an alkali metal hydroxide, and (2) 2-(substituted aryl)propionaldehyde is obatined in very high purity and high yield by contacting the reaction mixture of the above (1) containing the epoxypropane compound with anhydrous magnesium chloride, or contacting the epoxpropane compound in the presence of a soft nucleophile such as thioanisole with anhydrous magnesium chloride, whereby the isomerization proceeds rapidly under mild condition such as room temperature.

This invention has been completed on the basis of the above new findings.

One aspect of the invention is directed to a method for producing a 2-(substituted aryl)propionaldehyde represented by the formula,

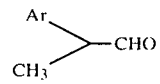

(wherein Ar denotes

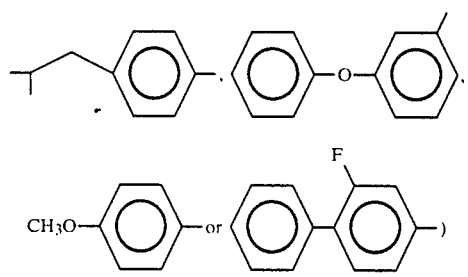

which comprises reacting a methyl (substituted aryl) ketone represented by the formula,

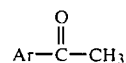

(wherein Ar is the same as mentioned above) with phenyldimethylsulfonium methylsulfate of the formula,

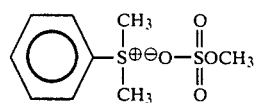

to produce a 2-(substituted aryl)-1,2-epoxypropane of the formula,

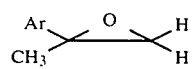

(wherein Ar is the same as defined above), and subjecting the epoxypropane compound, in the presence of thionisole contained in the reaction mixture, to contact with anhydrous magnesium chloride.

Another aspect of the present invention is directed to a method for producing the above-mentioned 2-(substituted aryl)propionaldehyde which comprises reacting a 2-(substituted aryl)-1,2-epoxypropane of the formula,

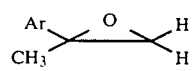

(wherein Ar is the same as defined above) with anhydrous magnesium chloride in the presence of a soft nucleophile.

The reaction formula is shown as follows:

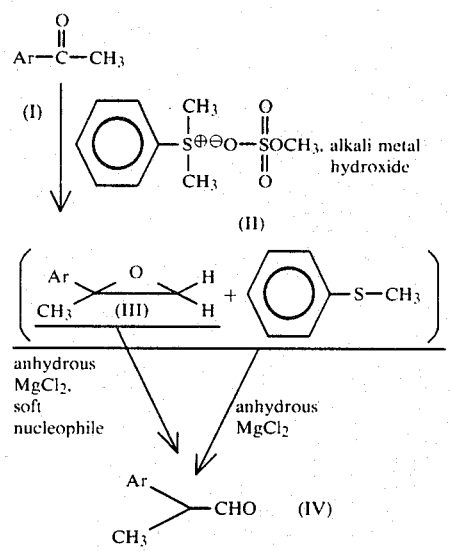

(wherein Ar is the same as defined above).

Phenyldimethylsulfonium methyl sulfate [II], which is employed in the first process of the invention, can be prepared quantitatively by reacting 1 to 1.1 mole of dimethyl sulfate per mole of thioanisole in the absence or presence of an inert solvent such as 1,2-dichloromethane, at 40° to 130° C., preferably 80° to 110° C., for scores of minutes to several hours, under heating and with stirring. The methyl sulfate [II] may be isolated from the reaction mixture, although it can be used in carrying out the method of the invention without such isolation. (First process)

In the practice of this process, the methyl sulfate [II] is preferably used in an amount of 1 to 1.3 moles per mole of the ketone [I]. The methyl sulfate [II] is dissolved or suspended in an appropriate solvent which is used in an amount of 1 to 10 parts by volume, preferably 2 to 5 parts by volume, per part by weight of the ketone [I] and, with stirring, the ketone [I] is added to the solution or suspension, followed by addition of an alkali metal hydroxide in an amount of 1 to 8 moles, preferably 1.5 to 4.5 moles, per mole of said ketone. The reaction is allowed to proceed with stirring.

The reaction temperature may be selected within a wide range of from a low temperature to the boiling point of the solvent employed but is preferably within the range of 0° to 70° C., more preferably 15° to 55° C.

Water-immiscible solvents such as halogenated hydrocarbons (e.g. dichloromethane, 1,2-dichloroethane) and hydrocarbons (e.g. toluene, xylene) may be employed as the reaction medium and this has a significant merit in practice of the invention. But water-miscible solvents such as dimethyl sulfoxide, acetonitrile and tetrahydrofuran can also be employed.

The use of water-immiscible solvents is advantageous in that they can be readily recovered for reuse by subjecting the reaction mixture to simple aftertreatment, for example washing with water and distillation. Among others, halogenated hydrocarbons are preferred because of good solubility of methyl sulfate [II] and easiness of recovery.

Sodium hydroxide and potassium hydroxide are preferred alkali metal hydroxides. They can be used in the form of an aqueous solution or preferably in a solid form.

The reaction time can be shortened by using a powder-form alkali metal hydroxide in a water-free solvent and by adding an accelerator, 2,6-di-t-butyl-4-methylphenol, in a catalyst-like amount.

In the above-mentioned reaction, 2-(substituted aryl)-1,2-epoxypropane can be produced quantitatively.

The reaction mixture preferably dehydrated, because it usually contains water as a by-product. Namely, the reaction mixture is added with a dehydrating agent such as anhydrous magnesium sulfate or anhydrous sodium sulfate, stirred at room temperature for a few minutes to several hours, and then the dehydrating agent is filtered off together with sodium methylsulfate originated from phenyldimethylsulfonium methyl sulfate.

The dehydrating agent may be used in an amount of 0.1 to 0.5 mole per mole of ketone [I].

The filtrate thus obtained is usually neutral, consisted of epoxypropane compound [III] and thioanisol originated from methyl sulfate [II] besides the reaction solvent, and can be employed as it is in the next reaction process without purification.

In the second reaction, preferably 0.05 to 0.5 mole, more preferably 0.1 to 0.2 mole, of anhydrous magnesium chloride per mole of the ketone [I] is added to the abovementioned mixture, and subjected to react with stirring.

The reaction temperature is preferably 0° to 60° C., more preferably 15° to 50° C. The reaction time relates to the reaction temperature and the amount of anhydrous magnesium chloride, however, the reaction can be completed usually within 1 to 10 and several hours.

The anhydrous magnesium chloride is preferably employed in the form of powder and particularly preferred is easily available powder of 100 mesh (Tyler).

In this reaction process, the epoxypropane compound [III] is isomerized by contact with the anhydrous magnesium chloride to the desired product [IV].

It was found that this reaction is accelerated by thioanisole existing in the reaction mixture of the former process.

According to an experiment performed by the present inventors, when 0.2 mole of anhydrous magnesium chloride is employed per mole of 2-(4-isobutylphenyl)-1,2-epoxypropane and stirred in dichloromethane at room temperature, only trace amount of the desired compound is formed along with by-products even after 8 hours of the reaction. On the other hand, when the above reaction is carried out in the presence of respective 0.2 mole and 1.0 mole of thioanisole, the reaction is completed after 8 hours and 3 hours, resulting in the desired propionaldehyde [IV] in high yield without accompanying by-product.

Thioanisole is a soft nucleohpile and it can be replaced by other soft nucleophile, for example, a sulfide such as dimethylsulfide, a thiol such as ethyl mercaptan, mercaptoethanol etc., and a phosphine such as triphenylphosphine. However, thioanisole is most preferable, because it is easy to handle.

Although it is difficult to settle suitable amount of the soft nucleophile, 0.1 to 0.2 mole of the nucleophile per mole of epoxypropane [II] may usually be employed to accomplish the purpose without hindrance, but it may also be employed in a large excess amount serving both as an accelerator and a solvent.

The reaction efficiency is to increase in proportion to the surface area of anhydrous magnesium chloride because it is a heterogenous reaction, however, the magnesium chloride is preferably employed in the form of easily available 100 mesh (Tyler) powder, as mentioned previously.

By the reaction of this process, 2-(substituted aryl)-propionaldehyde [IV] is produced in high yield.

The product compound [IV] may easily be separated from the reaction mixture by usual fractional distillation, because the compound is very stable to heat. For example, the reaction mixture is washed with water, the solvent in the mixture is distilled off by distillation under atmospheric or reduced pressure, and then the compound [IV] can be separated from the residue in high yield and high purity by distillation under reduced pressure.

When thioanisole is contained in the reaction mixture, the thioanisole can be quantitatively recovered in the above distillation and recycled to the first process as a raw material for producing phenyldimethylsulfonium methyl-sulfate.

In the following, this invention is further explained in the form of examples but it is not for a limitative purpose.

EXAMPLE 1

To a suspended solution of 165.2 g (0.66 mole) of phenyldimethylsulfonium methylsulfate in 300 ml of dichloromethane were added with stirring 105.7 g (0.6 mole) of 4-isobutylacetophenone and 0.1 g of 2,6-di-t-butyl-4-methylphenol, and then 48.0 g (1.2 mole) of powdered sodium hydroxide, followed by stirring for 30 minutes under cooling at 20° C. in a water bath.

The temperature of the mixture was raised gradually to 40°-45° C., and then the mixture was stirred for further 2.5 hours at the same temperature to complete the reaction. After cooling the reaction mixture to room temperature, 34.1 g (0.24 mole) of anhydrous sodium sulfate was added thereto. The mixture was strirred for 1.5 hours and filtered to remove insoluble materials which were, then, washed with a small quantity of dichloromethane. The washings were combined with the above filtrate. The combined solution was poured into a reaction vessel, anhydrous magnesium chloride powder [100 mesh (Tyler)] was added thereto and refluxed for 1.5 hours to complete the reaction. After cooling, the reaction mixture was washed with dilute hydrochloric acid and then aqueous sodium hydrochloride, and subjected to distillation under atmospheric pressure to distill dichloromethane. The remaining residue was further subjected to distillation under reduced pressure, whereby, after recovering thioanisole distilled at 72°-73° C. (8 mmHg), 105.5 g of 2-(4-isobutyl-phenyl)propionaldehyde distilled at 127°-129 °C. (8 mm Hg) was obtained as anhydrous, colorless oil. Yield; 92.5%, purity; above 99% (by GC analysis).

NMR (in CDCl₃) ppm:
0.90 (6H, d, J=6 cps,

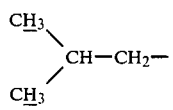

1.39 (3H, d, J=7 cps,

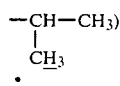

1.84 (1H, m,

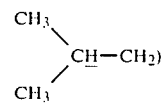

2.44 (2H, d, J=7 cps,

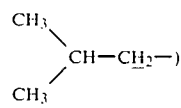

3.57 (1H, q, d, J=7,1, cps,

7.08 (4H, s, arom),
9.60 (1H, d, J=1 cps, —C$\underline{H}$O).
IR: $\nu_{C=O}$ 1730 cm⁻¹ (Neat).

EXAMPLE 2

To 24.8 g of thioanisole heated to 90° C., 27.8 g of (0.22 mole) of dimethylsulfate was added dropwise with stirring over 30 minutes, while maintaining its temperature at 90°-95° C. Stirring of the mixture at the same temperature for 30 minutes resulted in quantitative formation of phenyldimethylsulfonium methylsulfate (sulfonium salt) which formed a solid mass at room temperature. The solid mass was dissolved in 110 ml of hot dichloromethane, then cooled to 0° C. with stirring to afford a suspended solution of the sulfonium salt which was employed in the following reaction.

To the suspension was added with stirring 31.7 g (0.18 mole) of 4-isobutylacetophenone, 0.5 g of 2,6-di-t-butyl-4-methylphenol, and then, 16.0 g (0.4 mole) of powdered sodium hydroxide while cooling the mixture to 20° C. in a water bath. The mixture was gradually warmed up to 35°-40° C., and then stirred for 3 hours at the same temperature to complete the reaction.

The reaction mixture was cooled to room temperature, 7.2 g (0.06 mole) of anhydrous magnesium sulfate was added thereto, stirred for 1 hour, and then, filtered under reduced pressure to remove insoluble materials which was then washed with small quantity of dichloromethane. The washings were combined with the above filtrate. The combined solution was poured into a reaction vessel, 3.8 g (0.04 mole) of anhydrous magnesium chloride powder [100 mesh (Tyler)] was added thereto and stirred for 8 hours at room temperature to complete the reaction.

The reaction mixture thus obtained was treated in the same manner as in Example 1 to give 31.8 g of 2-(4-isobutylphenyl)propion aldehyde. (Yield; 93.0%, Purity; above 99.0%)

EXAMPLE 3

Phenylmethylsulfonium methylsulfate prepared in the same manner as in Example 2 from 74.5 g (0.6 mole) of thioanisole and 75.5 g (0.6 mole) of dimethylsulfate were added to 370 ml of dichloromethane to give a suspended solution. To the suspension, were added and dissolved 106 g (0.6 mole) of 3-phenoxyacetophenone, 250 mg of 2,6-di-t-butyl-4-methyl-phenol and 40 g (1.0 mole) of powdered sodium hydroxide, and then, stirred for 20 minutes under cooling in a water bath. The temperature of the mixture was raised to 40°–45° C., and the mixture was stirred for further 2.5 hours at the same temperature to complete the reaction. The reaction mixture was cooled to room temperature, 24 g (0.2 mole) of anhydrous magnesium sulfate was added thereto, stirred for 1 hour, and then filtered to remove insoluble materials which were then washed with small quantity of dichloromethane. The washings were combined with the above filtrate.

The combined solution was poured into a reaction vessel, 8.57 g (0.09 mole) of anhydrous magnesium chloride powder [100 mesh (Tyler)] was added thereto and stirred for 8 hours at room temperature to complete the reaction. The reaction mixture was filtered to remove insoluble materials and the filtrate was washed with aqueous sodium chloride and subjected to distillation under atmospheric pressure to distill off dichloromethane.

The remaining residue was subjected to further distillation under reduced pressure, whereby, after recovering thioanisole distilled at 50°–52° C. (4 mmHg), 104.8 g of 2-(3-phenoxyphenyl)propionaldehyde distilled at 139°–141° C. (3.5 mmHg) was obtained as colorless oil. (Yield; 92.7%, Purity; 99%).

NMR (in CDCl$_3$)ppm: 1.38 (3H, d, J=7 cps, —C$\underline{H}_3$), 3.52 (1H, q, d, J=7,1 cps,

6.67–7.45 (9H, m, arom), 9.55 (1H, d, J=1 cps, —C$\underline{H}$O).
IR: νc=o 1726 cm$^{-1}$ (Neat).

EXAMPLE 4

Phenyldimethylsulfonium methylsulfate prepared in the same manner as in Example 2 from 74.5 g (0.6 mole) of thioanisole and 75.5 g (0.6 mole) of dimethylsulfate were added into 260 ml of dichloromethane to give a suspended solution. To the suspension were added and dissolved 75.1 g (0.5 mole) of 4-methoxyacetophenone, 0.25 g of 2,6-di-t-butyl-4-methylphenol and 40.0 g (1.0 mole) of powdered sodium hydroxide and stirred for 20 minutes under cooling in a water bath. The temperature of the mixture was raised to 40°–45° C., and the mixture was stirred for further 3.5 hours at the same temperature to complete the reaction. The mixture was cooled to room temperature, 24 g (0.2 mole) of anhydrous magnesium sulfate was added thereto, stirred for 1 hour, and then filtered to remove insoluble materials which were, then, washed with small quantity of dichloromethane. The washings were combined with the above filtrate. The combined solution was poured into a reaction vessel, 8.57 g (0.09 mole) of anhydrous magnesium chloride powder [100 mesh (Tyler)] was added thereto and stirred for 8 hours at room temperature to complete the reaction. The reaction mixture was washed with dilute hydrochloric acid and then aqueous sodium chloride, and subjected to distillation under atmospheric pressure to distill off dichloromethane.

The remaining residue was subjected to further distillation under reduced pressure, whereby, after recovering thioanisole distilled at 50°–52° C. (4 mmHg), 69.8 g of 2-(4-methoxyphenyl)propionaldehyde distilled at 96° C. (3.5 mmHg) was obtained as colorless oil. (Yield; 85.0%, Purity; 98.5%).

NMR (in CDCl$_3$): 1.38 (3H, d, J=7 cps,

3.52 (1H, q, d, J=7,1 cps,

3.74 (3H, s, C$\underline{H}_3$O—), 6.6–7.4 (4H, m, arom), 9.54 (1H, d, J=1 cps, —C$\underline{H}$O).
IR: νc=o 1717 cm$^{-1}$ (Neat).

EXAMPLE 5

Phenyldimethylsulfonium methylsulfate prepared in the same manner as in Example 2 from 74.5 g (0.6 mole) of thioanisole and 75.5 g (0.6 mole) of dimethylsulfate was added into 300 ml of dichloromethane to give a suspended solution. To the suspension were added and dissolved 107.1 g (0.5 mole) of 4-acetyl-2-fluorobiphenyl, 0.25 g of 2,6-di-t-butyl-4-methylphenol and 40.0 g (1.0 mole) of powdered sodium hydroxide. The mixture was stirred for 2.5 hours at 40°–45° C. to complete the reaction. The mixture was cooled to room temperature, 2.4 g (0.2 mole) of anhydrous magnesium sulfate was added thereto, stirred for about 1 hour and filtered to remove insoluble materials which were, then, washed with small quantity of dichloromethane. The washings were combined with the above filtrate. The combined solution was poured into a reaction vessel, 7.14 g (0.075 mole) of anhydrous magnesium chloride powder [100 mesh (Tyler)] was added thereto and refluxed with stirring for 3 hours to complete the reaction.

After cooling, the reaction mixture was filtered to remove insoluble materials. The filtrate was washed with dilute hydrochloric acid and then aqueous sodium chloride, and subjected to distillation under atmospheric pressure to distill off dichloromethane.

The remaining residue was subjected to further distillation under reduced pressure to recover thioanisole distilled at 50°–52° C. (14 mmHg). The remaining residue was subjected to column chromatography on silica gel (n-hexane-toluene) to afford 96.4 g of 2-(2-fluoro-4-bisphenyl)propionaldehyde as colorless oil (Yield; 84.5%, Purity; 97.5%).

NMR (in CDCl$_3$)ppm: 1.36 (3H, d, J=7 cps, —C$\underline{H}_3$), 3.45 (1H, q, d, J=7,1 cps,

6.55–7.90 (8H, m, arom), 9.50 (1H, d, J=1 cps, —C$\underline{H}$O).
IR: νc=o 1720 cm$^{-1}$ (Neat).

EXAMPLE 6

To a stirred suspended solution of 50.1 g (0.2 mole) of phenyldimethylsulfonium methylsulfate in 100 ml of dichloromethane, was added 31.7 g (0.18 mole) of 4-isobutylacetophenone and 16.0 g (0.4 mole) of powdered sodium hydroxide. The mixture was stirred for 8 hours at 25°–35° C., and then added with water and stirred, followed by allowing to stand to form two layers.

The resulting organic layer was separated, washed with water until neutraland distilled under atmospheric pressure to remove dichloromethane. The remaining residue was subjected to fractional distillation under reduced pressure to recover nearly quantatively thioanisole distilled at 43°–45° C. (1 mmHg) and then 32.9 g of 2-(4-isobutylphenyl)-1,2-epoxypropane distilled at 58°–61° C. (0.15 mmHg) in 96.1% yield (on the basis of 4-isobutylacetophenone) as colorless oil.

REFERENCIAL EXAMPLE

The same procedure as in Example 6 was carried out except for employing 64.0 g (0.8 mole) of 50% aqueous sodium hydroxide in place of powdered hydroxide. The resulted reaction mixture was analyzed by gas chromatography and it was found that the ratio of 2-(4-isobutylphenyl)-1,2-epoxypropane to isobutylacetophenone in the mixture is 2:3.

EXAMPLE 7

24.8 g (0.2 mole) of thioanisole was heated to 90° C. with stirring and 27.8 g (0.22 mole) of dimethyl sulfate was added dropwise thereto over a period of 30 minutes keeping the temperature between 90 ° and 95° C. After the stirring was continued for an additional 30 minutes at the same temperature, the reaction mixture was cooled to room temperature to give phenyldimethylsulfonium methylsulfate quantitatively as solid mass.

The solid mass was dissolved in 110 ml of hot dichloromethane and then cooled with stirring to give a suspended solution of the sulfonium salt and subjected to the following reaction.

To the suspension was added 31.7 g (0.18 mole) of p-isobutylacetophenone and 14.4 g (0.36 mole) of powdered sodium hydroxide and the mixture was refluxed for 2 hours with stirring.

The reaction mixture was worked up in the same manner as described in Example 6 to afford 31.7 g of 2-(4-isobutylphenyl)-1,2-epoxypropane in 92.6% yield.

EXAMPLE 8

To a stirred suspended solution of 50.1 g (0.2 mole) of phenyldimethylsulfonium methylsulfate in 100 ml of 1,2-dichloroethne, was added 31.7 g (0.18 mole) of p-isobutylacetophneone and 16.0 g (0.4 mole) of powdered sodium hydroxide, followed by stirring for 10 hours at 30°–40° C. The reaction mixture was worked up in the same manner as described in Example 6 to afford 33.0 g og 2-(4-isobutylphenyl)-1,2-epoxypropane in 96.4% yield.

EXAMPLE 9

24.8 g (0.2 mole) of thioanisole was heated to 90° C. with stirring, 27.8 g (0.22 mole) of dimethyl sulfate was added thereto at 90°–95° C. over a period of 30 minutes and stirred for another 30 minutes at the same temperature. To the reaction mixture, 100 ml of toluene was added portionwise so as to maintain the temperature above 80° C. and then the mixture was cooled gradually with stirring to afford a suspension of phenyldimethylsulfonium methylsulfate in quantititative yield. To the suspension, 26.4 g (0.15 mole) of p-isobutylacetophenone and 16.0 g (0.4 mole) of powdered sodium hydroxide was added and the mixture was stirred for 8 hours at 50° C. The reaction mixture was worked up in the same manner as described in Example 6 to afford 24.7 g of 2-(4-isobutylphenyl)-1,2-epoxypropane in 86.7% yield.

EXAMPLE 10

To a solution of 38.0 g (0.2 mole) of 2-(4-isobutylphenyl)-1,2-epoxypropane in 130 ml of dichloromethane was added 3.43 g (0.036 mole) of anhydrous powdered (100 mesh, Tyler) magnesium chloride and 5.0 g (0.04 mole) of thioanisole and the mixture was stirred for 10 hours at room temperature. The reaction mixture was washed with dilute hydrochloric acid and then with aqueous sodium chloride several times until neutral, and subjected to distillation under atmospheric pressure to remove dichloromethane. The resulted residue was distilled under reduced pressure to afford 37.4 g of 2-(4-isobutylphenyl)propionaldehyde as colorless oil distilled at 127°–130° C. (8 mmHg). The yield is 98.5%

The purity is above 99.0% (by G. C. analysis).

NMR (in CDCl$_3$) ppm: 0.90 (6H, d, J=6 cps,

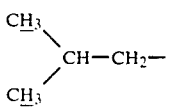

1.39 (3H, d, J=7 cps,

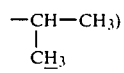

1.84 (1H, m,

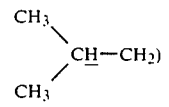

2.44 (2H, d, J=7 cps,

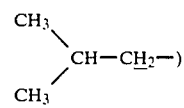

3.57 (1H, q, d, J=7,1, cps,

7.08 (4H, s, arom), 9.60 (1H, d, J=1 cps., —CHO).

IR: $\nu_{C=O}$ 1730 cm$^{-1}$ (Neat).

EXAMPLE 11

To a solution of 38.0 g (0.2 mole) of 2-(4-isobutylphenyl)-1,2-epoxypropane in 130 ml of dichloromethane was added 2.67 g (0.028 mole) of anhydrous powdered (100 mesh, Tyler) magnesium chloride and 5.0 g (0.04 mole) of thionisole, and the mixture was refluxed with stirring for 3 hours. After cooling the reaction mixture, insoluble materials were filtered off and washed with small amount of dichloromethane and the washings were combined with the filtrate. The combined solution was washed with aqueous sodium chloride and subjected to distillation under atmospheric pressure to remove dichloromethane. The remaining residue was subjected to distillation under reduced pressure to obtain 36.8 g of 2-(4-isobutylphenyl)propionaldehyde distilled at 127°–129° C. (8 mmHg) as colorless oil. Yield; 96.8%, purity; above 99%.

We claim:

1. A method for producing a 2-(substituted aryl)-propionaldehyde represented by the formula,

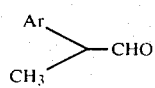

(wherein Ar denotes

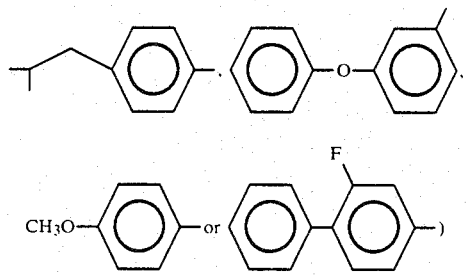

which comprises reacting a methyl (substituted aryl)ketone represented by the formula,

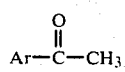

(wherein Ar is the same as defined above), with phenyldimethylsulfonium methylsulfate of the formula,

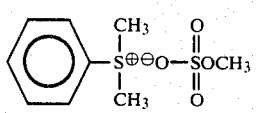

to produce a 2-(substituted aryl)-1,2-epoxypropane of the formula,

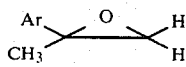

(wherein Ar is the same as defined above), in the presence of alkali metal hydroxide and subjecting the epoxypropane compound, in the presence of thioanisole contained in the above reaction mixture, to contact with anhydrous magnesium chloride.

2. A method according to claim 1 wherein the reaction mixture containing the epoxypropane compound and the thioanisole is contacted with anhydrous magnesium chloride.

3. A method according to claim 1 wherein the reaction mixture is dried and then contacted with anhydrous magnesium chloride.

4. A method according to claim 1 wherein the magnesium chloride is employed in the form of 100 mesh (Tyler) powder.

5. A method for producing a 2-(substituted aryl)-propionaldehyde represented by the formula

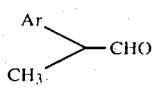

(wherein Ar denotes

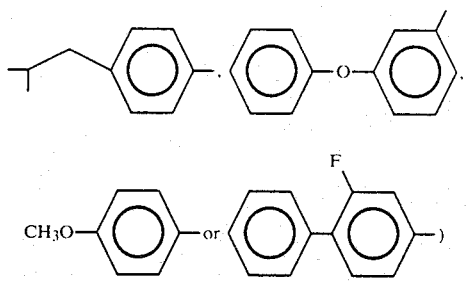

which comprises reacting a 2-(substituted aryl)-1,2-epoxypropane of the formula

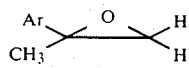

(wherein Ar is the same as defined above) with anhydrous magnesium chloride in the presence of at least one member selected from the group consisting of thioanisole, dimethylsulfide, ethyl mercaptan, mercaptoethanol or triphenylphosphine.

6. A method according to claim 5 wherein said member is dimethylsulfide.

7. A method according to claim 5 wherein said member is thioanisole.

8. A method according to claim 5 wherein the anhydrous magnesium chloride is employed in the form of 100 mesh (Tyler) power.

9. A method accoding to claim 5 wherein the epoxypropane compound is contacted with anhydrous magnesium chloride in a molar ratio of 1:0.05 to 1:1, preferably 1:0.1 to 1:0.3.

10. A method according to claim 1 wherein Ar represents:

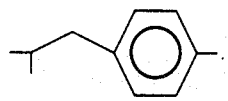

11. A method according to claim 1 wherein Ar represents:

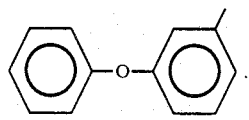

12. A method according to claim 1 wherein Ar represents:

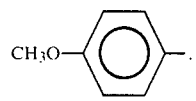
13. A method according to the claim 1 wherein Ar represents:
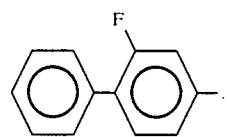
* * * * *